US008802124B2

(12) United States Patent  
Tenerz et al.

(10) Patent No.: US 8,802,124 B2  
(45) Date of Patent: Aug. 12, 2014

(54) ERODIBLE VESSEL SEALING DEVICE WITHOUT CHEMICAL OR BIOLOGICAL DEGRADATION

(75) Inventors: Lars Tenerz, Uppsala (SE); Dan Åkerfeldt, Uppsala (SE); Torbjörn Mathisen, Älvsjö (SE)

(73) Assignee: Radi Medical Systems AB, Uppsala (SE)

( * ) Notice: Subject to any disclaimer, the term of this patent is extended or adjusted under 35 U.S.C. 154(b) by 1747 days.

(21) Appl. No.: 10/513,688

(22) PCT Filed: Apr. 24, 2003

(86) PCT No.: PCT/SE03/00656
§ 371 (c)(1),
(2), (4) Date: Jan. 3, 2005

(87) PCT Pub. No.: WO03/094740
PCT Pub. Date: Nov. 20, 2003

(65) Prior Publication Data
US 2005/0169974 A1    Aug. 4, 2005

Related U.S. Application Data

(60) Provisional application No. 60/378,356, filed on May 8, 2002.

(51) Int. Cl.
| | |
|---|---|
| *A61B 17/00* | (2006.01) |
| *A61L 26/00* | (2006.01) |
| *A61L 17/10* | (2006.01) |
| *A61L 17/06* | (2006.01) |
| *A61K 9/00* | (2006.01) |
| *A61B 17/03* | (2006.01) |
| *A61B 17/08* | (2006.01) |
| *A61L 31/04* | (2006.01) |
| *A61L 31/14* | (2006.01) |
| *A61F 2/06* | (2013.01) |
| *A61B 17/064* | (2006.01) |

(52) U.S. Cl.
CPC ......... *A61B 17/0057* (2013.01); *A61L 26/0009* (2013.01); *A61L 17/10* (2013.01); *A61L 26/0061* (2013.01); *A61L 31/04* (2013.01); *A61L 17/06* (2013.01); *A61B 2017/00615* (2013.01); *A61B 2017/00778* (2013.01); *A61L 31/148* (2013.01); *A61K 9/0024* (2013.01); *A61L 31/042* (2013.01); *A61B 17/0643* (2013.01); *A61B 2017/00004* (2013.01); *A61B 2017/00659* (2013.01); *A61B 2017/0647* (2013.01)
USPC ...................................................... 424/426

(58) Field of Classification Search
None
See application file for complete search history.

(56) References Cited

U.S. PATENT DOCUMENTS

| | | | | |
|---|---|---|---|---|
| 3,653,383 | A | * | 4/1972 | Wise ............................ 604/364 |
| 3,791,388 | A | | 2/1974 | Hunter et al. |
| 4,690,684 | A | | 9/1987 | McGreevy et al. |
| 4,744,364 | A | | 5/1988 | Kensey |
| 4,838,280 | A | | 6/1989 | Haaga |
| 4,852,568 | A | | 8/1989 | Kensey |
| 4,890,612 | A | | 1/1990 | Kensey |
| 5,021,059 | A | | 6/1991 | Kensey et al. |
| 5,084,558 | A | * | 1/1992 | Rausch et al. ................ 530/385 |
| 5,282,827 | A | | 2/1994 | Kensey et al. |
| 5,342,393 | A | | 8/1994 | Stack |
| 5,350,399 | A | | 9/1994 | Erlebacher et al. |
| 5,358,677 | A | * | 10/1994 | Muth et al. ..................... 264/87 |
| 5,531,759 | A | | 7/1996 | Kensey et al. |
| 5,593,422 | A | | 1/1997 | Muijs Van De Moer et al. |
| 5,620,461 | A | | 4/1997 | Muijs Van De Moer et al. |
| 5,630,822 | A | | 5/1997 | Hermann et al. |
| 5,630,833 | A | | 5/1997 | Katsaros et al. |
| 6,325,789 | B1 | | 12/2001 | Janzen et al. |
| 6,361,551 | B1 | | 3/2002 | Torgerson et al. |
| 6,508,828 | B1 | | 1/2003 | Akerfeldt et al. |
| 6,596,012 | B2 | | 7/2003 | Akerfeldt et al. |
| 6,949,113 | B2 | | 9/2005 | Van Tassel et al. |
| 2001/0056254 | A1 | * | 12/2001 | Cragg et al. ..................... 604/15 |
| 2002/0006429 | A1 | | 1/2002 | Redmond et al. |
| 2003/0050667 | A1 | | 3/2003 | Grafton et al. |
| 2004/0093025 | A1 | | 5/2004 | Egnelov |

FOREIGN PATENT DOCUMENTS

| | | |
|---|---|---|
| EP | 0894474 A1 | 2/1999 |
| EP | 0474752 B2 | 12/2000 |
| EP | 1 169 968 B1 | 1/2002 |
| WO | WO 96/33673 A1 | 10/1996 |
| WO | WO 98/31286 A1 | 7/1998 |

(Continued)

OTHER PUBLICATIONS

Ebewele, R. O. Polymer Science and Technology, 2000, CRC Press, Boca Raton, FL.*
Oster, G. J. Pol. Sci. (1952). 9(6) p. 553-556.*
Wang M., Y. et al. Neurosurgery (2001), 49(4); 962-968.*
Dan Akerfeld et al., USPTO Office Action, U.S. Appl. No. 10/563,024, Mar. 10, 2010, 10 pages.
Dan Akerfeld et al., USPTO Office Action, U.S. Appl. No. 10/563,024, Jun. 25, 2009, 8 pages.
Dan Akerfeld et al., USPTO Office Action, U.S. Appl. No. 10/563,024, Oct. 14, 2008, 9 pages.
Dan Akerfeld et al., USPTO Office Action, U.S. Appl. No. 10/563,024, May. 30, 2008, 8 pages.
Dan Akerfeld et al., USPTO Office Action, U.S. Appl. No. 10/563,024, Sep. 28, 2007, 12 pages.

*Primary Examiner* — Kevin S Orwig
(74) *Attorney, Agent, or Firm* — Foley & Lardner LLP

(57) ABSTRACT

The present invention provides a dissolvable medical sealing device (3, 4; 6, 7; 9) for closing a wound in vessel. A sealing device (3, 4, 6, 7, 9) according to the invention is made of a material that dissolves by means of physical processes, rather than by means of chemical or biological processes. Such a sealing device (3, 4; 6, 7; 9) can be made of polyethylene glycol, polypropylene glycol, copolymers containing ethylene glycol and propylene glycol, polyvinyl alcohol or polyvinyl pyrolidone, or any combinations thereof.

22 Claims, 1 Drawing Sheet

(56) References Cited

FOREIGN PATENT DOCUMENTS

| WO | WO 98/31287 | A1 | | 7/1998 | |
|----|----|----|----|----|----|
| WO | WO 00/78226 | A1 | | 12/2000 | |
| WO | WO 01/40348 | A2 | | 6/2001 | |
| WO | WO 01/056475 | | * | 8/2001 | ............ A61B 17/00 |
| WO | WO 02/24114 | A2 | | 3/2002 | |

* cited by examiner

ERODIBLE VESSEL SEALING DEVICE WITHOUT CHEMICAL OR BIOLOGICAL DEGRADATION

FIELD OF THE INVENTION

The present invention relates to a wound closure device for closing a wound in a vessel, comprising a first sealing device adapted to be positioned against the inner surface of the vessel wall and a fastener adapted to keep the first sealing device in place.

BACKGROUND OF THE INVENTION

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like.

After completion of the medical procedure, there will be an incision or a wound in the wall of the blood vessel corresponding to the size of the introducer. The bleeding from the wound, which is the result of such a surgical operation, can be stopped by applying direct pressure on the wound. However, applying direct pressure on the wound will require assistance of additional medical personnel and may also restrict the flow of blood through the vessel.

Another, more sophisticated, basic method for sealing such a percutaneous puncture in a vessel involves the positioning of an intra-arterial occluder against the inner wall of the vessel. Different examples of this basic method may be found in U.S. Pat. Nos. 4,852,568; 4,890,612; 5,021,059; 5,350,399 and 5,593,422. The intra-arterial occluder can be held taut against the inner vessel wall by a filament or suture only, as described in U.S. Pat. No. 4,852,568, or an extra-arterial occluder can be threaded over the suture and positioned against the outer wall of the vessel to secure the intra-arterial occluder, as disclosed in U.S. Pat. No. 5,593,422. In U.S. Pat. Nos. 4,890,612 and 5,021,059, the intra-arterial occluder, which is positioned by means of a suture or a filament, is supplemented with a plug, which is positioned in the puncture channel. The sealing device disclosed in U.S. Pat. No. 5,350,399 comprises an intra-arterial occluder and an extra-arterial occluder.

The different materials from which these intra-arterial and/or extra-arterial occluders are made are not the main subject matters of the inventions disclosed in the patents above. Usually, the material for such an occluder is characterized as being a resorbable or absorbable, biocompatible or biodegradable material. In U.S. Pat. Nos. 4,890,612 and 4,852,568, a preferred material for the occluder is GELFOAM, a gelatin sold by Johnson & Johnson, while a suggested material in U.S. Pat. No. 5,021,059 is MEDISORB, a resorbable lactide/glycolide polymer sold by E.I. DuPont de Nemours, Inc. In a preferred embodiment of the invention according to U.S. Pat. No. 5,593,422, the occluder is made from a material that comprises collagen or alginate. It is well known in the art that the materials used in these types of occluders degrade inside the body by means of biological and/or chemical processes. This means that the materials, which are often based on a polymeric structure, undergo reaction as they degrade and are absorbed. Such reactions can be, for example, hydrolysis including hydrolysis mediated by enzymes. The biological and chemical degradation processes typically lower the molecular weight of the polymeric structure, which increases solubility and absorbability. Furthermore, for these types of occluders, it is equally well known in the art that the degradation time, i.e. the time it takes for the body to absorb an occluder made of the material in question, typically is several weeks, months or even years. U.S. Pat. No. 5,593,422 gives a degradation time of a few weeks, while U.S. Pat. No. 4,890,612 mentions a degradation time of approximately 45 days. U.S. Pat. No. 5,350,399 discloses that degradable materials should "slowly dissolve". Additional background on absorbable materials is set forth in WIPO Publication WO 01/40348.

One reason for using an absorbable material in an occluder is to avoid or minimize the risk of having an inflammatory response in the tissue surrounding the occluder. This inflammation can be the result of a mechanical damage on the vessel wall caused by mechanical wearing of the occluder during the natural movements of the vessel. From this point of view, the shorter time before the complete degradation of an occluder, the less is the risk of having an inflammation in the tissue surrounding the occluder. In this context it should be noted that when only external pressure is applied on the puncture wound, i.e. without using any of the intra-arterial or extra-arterial occluders described above, the actual compression time can be as short as fifteen minutes, although the patient usually is kept immovable for a few hours. This means that the occluders known in the state of the art remain in the body an unduly long time. If another medical operation is going to be performed at the same operation site as the first operation, it is a disadvantage to have an occluder already inserted in the vessel, since this occluder can obstruct the medical operation itself and may also make it impossible to safely position a new occluder at (or near) the same position.

A problem with the materials of these known seals is that different parts of the seals will be in different states of degradation during the absorption process. Therefore the seals become increasingly porous and will exhibit lower rupture strength, and due to the blood flow in the vessel there is a risk that pieces of different sizes of the seal come loose and follow the blood flow to more narrow passages where the parts can get stuck and restrict or even prevent the blood flow. Of course this could be serious for the patient and may necessitate an operation.

Furthermore, a suture or filament that is holding the seal in place is rather thin in comparison with a seal and thus there is a risk that the suture or filament ruptures through a seal being in more or less degraded state. Also in such case the seal will come loose in the vessel where it can follow the blood flow as described above.

A further problem with the known seals is that around the seal cells and tissues develop on and adhere to the surface, so that the seal becomes encapsulated in a sac-like tissue material. Inside the sac-like encapsulating tissue, the seal degrades. Then the sac-like encapsulating material also regresses. For a conventional seal, this means that the seal and the tissue that develops thereon occupy more and more of the available space inside the vessel until the process is reversed, i.e. when seal starts to degrade and the encapsulating tissue starts regress. Furthermore, this problem may be enhanced by the fact that many conventional seals are made of materials that swell in the fluid inside a vessel. The ingrowth of the encapsulating tissue can restrict blood flow temporarily or even permanently, particularly if the encapsulating tissue fails to regress properly. Also, if the tissue does not grow on the surface of a conventional seal, then the seal can potentially come loose inside the blood vessel.

The encapsulating of the seal is needed in the known seals described above. Without the encapsulation the breaking down of the seal would probably cause parts of the seal to come loose and drift away with the blood flow. Thus the known seals rely on the encapsulating effect. However, it is not safe to rely on this effect since it could vary between individuals, and furthermore even small rests of certain materials, such as Teflon®, from the manufacturing of the seal could be left on the surface of the seal and prevent the adhering of the cells.

SUMMARY OF THE INVENTION

An object of the invention is to provide a safe and reliable wound closure device not causing problems to the patient.

This is achieved in a wound closure device for closing a wound in a vessel, comprising a first sealing device adapted to be positioned against the inner surface of the vessel wall and a fastener adapted to keep the first sealing device in place. Where the first sealing device is made of a material that dissolves by means of physical processes.

Hereby tissue ingrowth and cell adhesion is minimal or substantially does not occur as the seal surface is being eroded and/or dissolved away continuously. In other words, the seal surface is being constantly peeled off by the blood flow. Hereby there is no risk that the seal becomes larger and limits the blood flow.

Preferably the material dissolves fast, suitably in less than seven days.

Hereby the seal dissolves inside the vessel (or outside the vessel in the case of an extra-arterial occluder) after a few days and the seal is not left inside the vessel an unnecessary long time. This gives a safe seal since the inflammatory risk is reduced with a short dissolution time. Furthermore, with a short dissolution time parts of the seal that accidentally come loose in the blood flow will soon be dissolved and would not cause any problems for the patient in this short time. The adherence of cells and tissues on the seal is also even more unlikely when the material dissolves fast.

The sealing devices are generally hydrolytically stable and do not chemically or biologically degrade in the functional use of the sealing device. Herein, the terms "dissolve", "dissolution" or "dissolvable" refer to a process in which physical interactions between molecules are broken, without breaking of covalent bonds as the molecules, typically polymer chains, swell and dissolve into the surrounding medium, such as the aqueous media within and external to vessels. Swelling and dissolution in aqueous media outside the body can be used as an in vitro test to simulate the in vivo dissolution. This is in contrast to the known sealing devices described above, which degrade at least partly by means of biological and/or chemical processes, in which chemical bonds, usually covalent bonds, within a single polymer or between polymer molecules need to be broken before the dissolution process can commence.

The present invention overcomes the disadvantages of having an unnecessarily long degradation time encountered in arterial sealing devices made of an absorbable material that at least partly degrades by means of biological and/or chemical processes. The invention provides a sealing device that can be made of a material that dissolves inside a vessel (or outside the vessel in the case of an extra-arterial occluder) by physical processes. This reduces the time during which the sealing device is present in the body to a few days.

DESCRIPTION OF THE INVENTION

Figure 1:
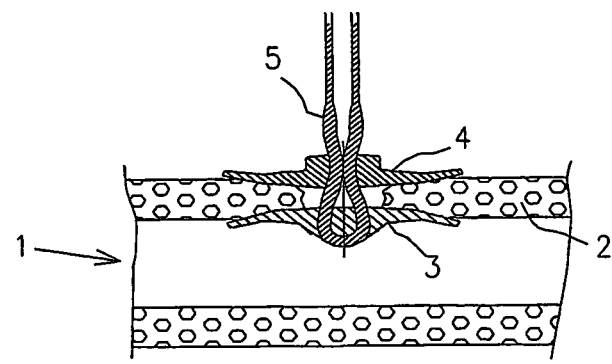
FIG. 1 is a schematic cross-sectional view of a first embodiment of a sealing device comprising an intra-arterial occluder and an extra-arterial occluder, which are connected by a filament.

In FIG. 1 is shown a portion of a vessel 1 in a living body, whether a human or animal body, such as the femoral or radial artery. A puncture has been made through the vessel wall 2, thereby creating an opening, which has to be occluded after the treatment that made the puncture necessary. In FIG. 1, a first embodiment of a wound closure device according to the present invention has been positioned to close the puncture wound. The wound closure device comprises a first sealing device 3, which is positioned against the inner surface of the vessel wall 2, and a second sealing device 4, which is positioned against the outer surface of the vessel wall 2. The wound closure device also comprises a fastener 5 in the form of a multifilament 5, which holds the first and second sealing devices 3, 4 together by means of friction locking.

Figure 2:
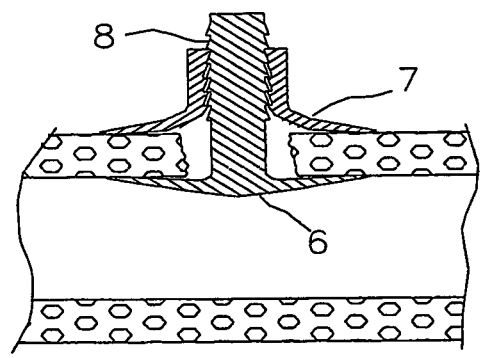
FIG. 2 illustrates a second embodiment of a sealing device comprising an intra-arterial occluder and an extra-arterial occluder, which are held together by a saw-toothed guide extending integrally from the intra-arterial occluder.

A second embodiment of a wound closure device according to the present invention is illustrated in FIG. 2. The wound closure device comprises a first sealing device 6, which is positioned against the inner surface of the vessel wall, and a second sealing device 7, which is positioned against the outer surface of the vessel wall. In this embodiment, the first and second sealing devices 6, 7 are held together by a saw-toothed guide 8, which extends integrally from the first sealing device 6.

Figure 3:
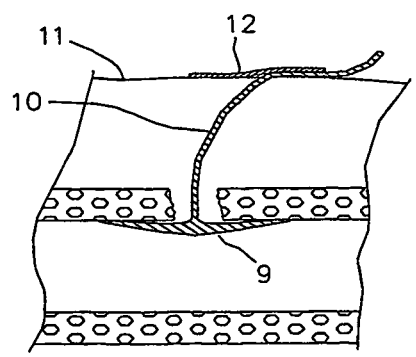
FIG. 3 illustrates a third embodiment of a sealing device comprising an intra-arterial occluder, which is kept in position by a filament.

FIG. 3 illustrates a third embodiment of a wound closure device according to the present invention. The closure device shown in FIG. 3 comprises a sealing device 9, through which a suture 10 is threaded. In use, the sealing device 9 is urged toward the inner surface of the vessel wall by simply pulling the suture 10. In order to hold the sealing device 9 in place, the suture is then held and is secured in position on the patient's skin 11, such as by use of a strip of conventional tape 12.

As mentioned above, sealing devices of the types shown in FIG. 1 to FIG. 3 are conventionally made from materials that are described as being absorbable or biodegradable. Such sealing devices degrade by biological or chemical processes, in which covalent bonds in the molecules of the materials are broken. This can mean, for example, that a polymeric material is hydrolysed so that its molecular weight is reduced. Because of these relatively slow degradation processes, the corresponding degradation times may be as long as several weeks, months or even years. A degradation time of several weeks is usually not motivated by any medical necessity, since it normally takes only about fifteen minutes before the bleeding from the puncture wound has stopped, and even for patients with longer healing times, such as patients treated with heparin or other drugs that inhibit blood clotting, the healing time is only a few hours. Further, as mentioned earlier, a long degradation time involves, inter alia, a increased risk of having an inflammation in the tissue surrounding the sealing device.

Consequently, the invention provides a sealing device made from a material that dissolves by means of physical processes in which physical interactions between the molecules of the material, typically polymer chains, are broken as the material dissolves, thereby being characterized by a relatively short dissolution time, which may be as short as less than about seven days, more particularly, less than about three days, or more particularly, about one or two days. Dissolution can occur and be enhanced by dynamic exposure to aqueous media such as by erosion from blood flow wear on the material. The materials are hydrolytically stable in that, although soluble, they are not hydrolysed or subject to chemical or biological degradation. The sealing devices 3, 4, 6, 7, 9 shown in FIG. 1 to FIG. 3 are made of materials that dissolve by such physical processes. For example, the seal can comprise at least 90 weight percent of the material that dissolves from physical processes without chemical or biological degradation. These materials can be synthetic or natural. They can be amorphous, semi-crystalline, or crystalline, although in a general crystallinity may slow down the dissolution rate. In particular, the can be hydrophilic, water-soluble polymers including, for example, polymers which contain ionic groups and/or hydrophilic oxygen- or nitrogen-containing groups including amino, amide, ether, carbonyl, hydroxyl, carboxylic acid, carboxylate, phosphonic acid, phosphonate, sulfonic acidsulfonate, and esters, as well as derivates and salts thereof. Examples of such materials are materials made of polyethylene glycol, polypropylene glycol, copolymers containing ethylene glycol and propylene glycol (so called Pluronics®), polyvinyl alcohol or polyvinyl pyrolidone, salt, sugar, or any combinations thereof. Other examples include polyacrylic acid, polysaccharides, polyamines, quaternary ammonium polymers, associative thickeners, polyvinyl methyl ether-maleic anhydride, carboxypolymethylene, and hydroxyalkyl cellulose ethers. Natural polymers including xanthan gums, guar gum and derivates, pectin, tree and shrub exudates, and seaweed-based polymers. Known polymer technology can be used in preparing the devices including, for example, use of blends, copolymers, additives, fillers, and surface modifications.

The dissolution time for a sealing device according to the present invention is less than about a week, preferably less than about three days. In practise, the actual dissolution time will, of course, depend not only on the specific choice of material but also on the configuration of the sealing device in question as well as the type of solvent, e.g. blood or urine, rate of fluid flow past the seal causing seal erosion, and other factors.

Generally, fasteners, such as fastener 5 and suture 10, are made of different material than the sealing devices (e.g. 3, 4, 6, 7, and 9) themselves; however the fasteners and sealing devices may be made of the same material. In general, the fastener should not dissolve significantly until after at least the inner sealing device has dissolved to prevent the inner sealing device from becoming loose in the artery. Alternatively, the fastener can be designed to be removed from the body after at least the inner seal has dissolved. The rate of dissolution can be controlled so that the fastener does not dissolve before the sealing device. The can be achieved by, for example, control of material selection, porosity, and geometry and/or by material profiling.

The sealing devices according to the present invention dissolve only or almost only by means of physical processes, wherewith it should be understood that the contributions to the degradation from any biological and/or chemical processes are negligible. This is in contrast to the sealing devices according to the state of art, where the reaction kinetics for the different chemical or biological processes with which the materials of the sealing device are degraded determine the degradation time.

Although the present invention has been described with reference to specific embodiments, also shown in the appended drawings, it will be apparent for those skilled in the art that many variations and modifications can be done within the scope of the invention as described in the specification and defined with reference to the following claims. Accordingly, the examples shown below are merely provided to illustrate the invention and should not be considered to limit the invention.

The invention claimed is:

1. An implantable wound closure device for closing a wound in a vessel, comprising:
   a first sealing device configured to be positioned against an inner surface of a wall of the vessel, and
   a fastener fastened to the first sealing device, wherein the fastener is configured to pass through the wound and to keep the first sealing device in place,
   wherein the first sealing device is made of a polymer material,
   wherein the first sealing device is configured to dissolve by erosion caused by physical processes occurring within the vessel without chemical or biological degradation,
   wherein, upon implantation, the first sealing device is configured to dissolve by erosion caused by the physical processes occurring within the vessel at at least one exposed surface of the first sealing device that is exposed to an interior of the vessel, and
   wherein the first sealing device consists of one or more of the following: polypropylene glycol, polyacrylic acid, polyvinyl methyl ether-maleic anhydride, xanthan gum, guar gum, and pectin.

2. An implantable wound closure device according to claim 1, further comprising a second sealing device made of a polymer material, adapted to be positioned against an outer surface of the wall of the vessel, and configured to dissolve by physical processes without substantial chemical or biological degradation.

3. An implantable wound closure device according to claim 1, wherein the first sealing device is configured to dissolve in water by erosion caused by physical processes without substantial chemical or biological degradation.

4. An implantable wound closure device according to claim 1, wherein the first sealing device is configured to start dissolving essentially immediately after positioning of the first sealing device within the vessel.

5. An implantable wound closure device according to claim 1, wherein the first sealing device is configured to dissolve in seven days or less after the implantation.

6. An implantable wound closure device according to claim 1, wherein the first sealing device is configured to dissolve in three days or less after the implantation.

7. An implantable wound closure device according to claim 1, wherein the first sealing device is configured to dissolve in 24 hours after the implantation.

8. An implantable wound closure device according to claim 1, wherein the first sealing device is water-soluble.

9. An implantable wound closure device according to claim 1, wherein the first sealing device comprises polypropylene glycol.

10. An implantable wound closure device according to claim 1, wherein the first sealing device is configured to erode due to blood flow wear on the first sealing device.

11. An implantable wound closure device according to claim 1, wherein the first sealing device is configured to dissolve inside the vessel after three days and before seven days.

12. An implantable wound closure device according to claim 1, wherein the first sealing device is configured to dissolve inside the vessel in less than seven days.

13. An implantable wound closure device according to claim 1, wherein the first sealing device and the fastener are made from different materials.

14. An implantable wound closure device according to claim 1, wherein the fastener is configured to dissolve later than the first sealing device after the first sealing device is implanted in the vessel.

15. An implantable wound closure device for closing a wound in a vessel, comprising:
- a first sealing device configured to be positioned against an inner surface of a wall of the vessel, and
- a fastener fastened to the first sealing device, wherein the fastener is configured to pass through the wound and to keep the first sealing device in place,
- wherein the first sealing device is made of a polymer material,
- wherein the first sealing device is configured to dissolve by erosion caused by physical processes occurring within the vessel without chemical or biological degradation,
- wherein, upon implantation, the first sealing device is configured to dissolve by erosion caused by the physical processes occurring within the vessel at at least one exposed surface of the first sealing device that is exposed to an interior of the vessel, and
- wherein the first sealing device comprises at least 90% by weight of one or more of the following: polypropylene glycol, polyacrylic acid, polyvinyl methyl ether-maleic anhydride, xanthan gum, guar gum, and pectin.

16. An implantable wound closure device according to claim 15, further comprising a second sealing device made from a polymer material, adapted to be positioned against an outer surface of the wall of the vessel, and configured to dissolve by physical processes without substantial chemical or biological degradation.

17. An implantable wound closure device according to claim 15, wherein the first sealing device is configured to dissolve in water by erosion caused by physical processes without substantial chemical or biological degradation.

18. An implantable wound closure device according to claim 15, wherein the first sealing device is configured to start dissolving essentially immediately after positioning of the first sealing device within the vessel.

19. An implantable wound closure device according to claim 15, wherein the first sealing device is configured to dissolve in three days or less after the implantation.

20. An implantable wound closure device according to claim 15, wherein the first sealing device is configured to erode due to blood flow wear on the first sealing device.

21. An implantable wound closure device according to claim 15, wherein the first sealing device is configured to dissolve inside the vessel after three days and before seven days.

22. An implantable wound closure device according to claim 15, wherein the first sealing device is configured to dissolve inside the vessel in less than seven days.

* * * * *